(12) United States Patent
Smerica et al.

(10) Patent No.: US 12,295,872 B2
(45) Date of Patent: May 13, 2025

(54) SINUS TRACT EXPANDER SYSTEM AND METHOD OF TREATMENT THEREBY

(71) Applicant: AbsorbENT, LLC, Houston, TX (US)

(72) Inventors: Abel Smerica, Conroe, TX (US); Joseph Edmonds, Houston, TX (US)

(73) Assignee: ABSORBENT, LLC, Houston, TX (US)

( * ) Notice: Subject to any disclaimer, the term of this patent is extended or adjusted under 35 U.S.C. 154(b) by 383 days.

(21) Appl. No.: 17/871,407

(22) Filed: Jul. 22, 2022

(65) Prior Publication Data

US 2024/0024147 A1 Jan. 25, 2024

(51) Int. Cl.
*A61F 5/08* (2006.01)
(52) U.S. Cl.
CPC ..................................... *A61F 5/08* (2013.01)
(58) Field of Classification Search
CPC ...... A61F 2002/0835; A61F 2002/0829; A61F 2002/30579; A61F 5/08; A61B 2017/0412; A61B 2017/0409; A61B 2017/0432; A61B 2017/0427; A61B 2017/0429; A61B 2017/043; A61B 2017/0433; A61B 2017/0435; A61B 17/8858
See application file for complete search history.

(56) References Cited

U.S. PATENT DOCUMENTS

| | | | |
|---|---|---|---|
| 6,129,763 A | 10/2000 | Chauvin et al. | |
| 2006/0259065 A1 | 11/2006 | Maryanka | |
| 2011/0112550 A1* | 5/2011 | Heaven | A61B 17/0401 606/151 |
| 2016/0100833 A1 | 4/2016 | Lunn et al. | |

OTHER PUBLICATIONS

International Search Report and Written Opinion issued in corresponding International Application No. PCT/US22/74059, mailed Oct. 17, 2022, Alexandria, Virginia.

* cited by examiner

*Primary Examiner* — Majid Jamialahmadi
(74) *Attorney, Agent, or Firm* — HAUPTMAN HAM, LLP

(57) ABSTRACT

A tract expander includes a base having a threaded central hole and a plurality of wings. The base and the wings are connected by a plurality of hinges. Each of the plurality of hinges is connected to the base and to a wing of the plurality of wings so that each wing moves relative to the base. A threaded shaft includes a tip. The tip diameter is larger than the threaded shaft diameter and the threaded shaft is configured to screw into the threaded central hole. The threaded shaft is configured to rotate and move the tip toward the hinged base, causing the tops of the plurality of wings to move away from the threaded shaft.

14 Claims, 17 Drawing Sheets

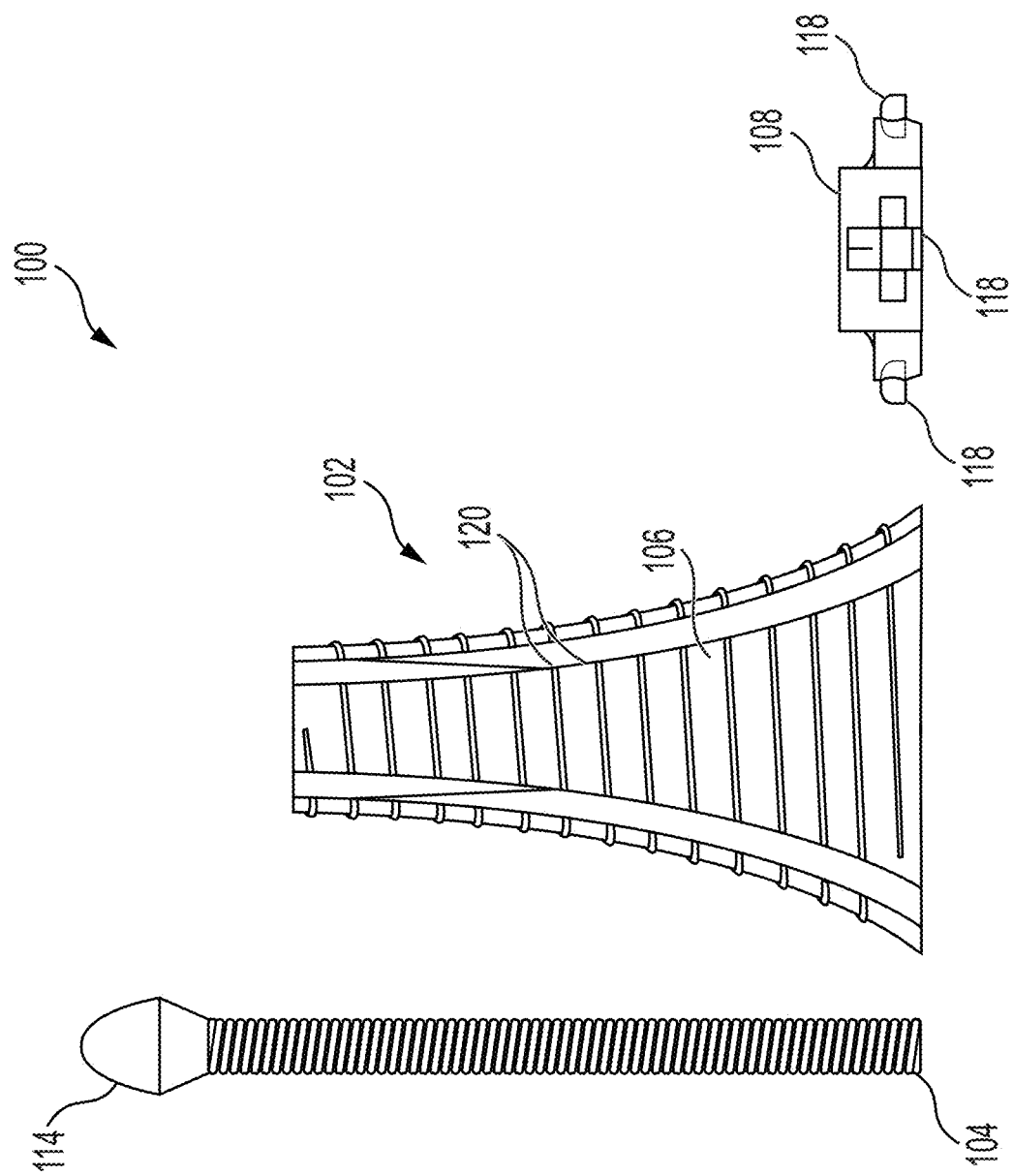

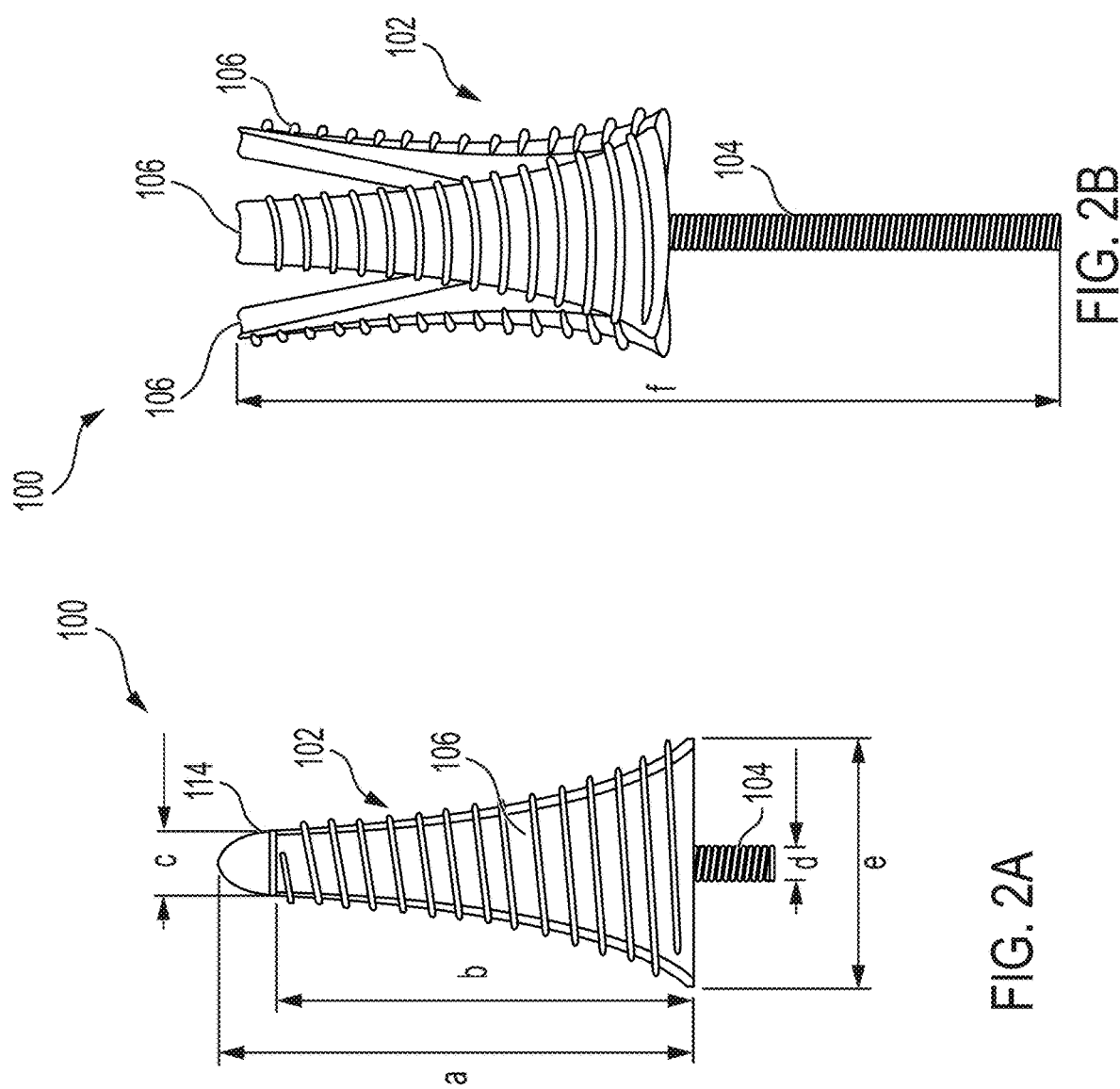

SINUS TRACT EXPANDER SYSTEM AND METHOD OF TREATMENT THEREBY

BACKGROUND

Patients suffer from medical conditions caused by narrow passages, canals and ducts, including sinus passages. To treat stenotic sinus issues, surgery is performed to enlarge the stenotic sinus tracts. However, after the sinus tracts have been opened, the healing process sometimes results in scar tissue, which again reduces the size of the afflicted nasal passage.

Balloon sinus dilation is used as a treatment for the stenotic sinus passages. The circumference of the sinus tract is increased over time by slowly increasing the pressure within a balloon inserted into the stenotic sinus passage. The increase in pressure increases the circumference of the balloon, causing the inflated balloon to apply pressure to the narrow sinus passage.

BRIEF DESCRIPTION OF THE DRAWINGS

FIG. 1A is a side view of the components of a sinus tract expander, in accordance with some embodiments.

FIGS. 2A and 2B are side views of a sinus tract expander, in accordance with some embodiments.

DETAILED DESCRIPTION

Figure 1B:
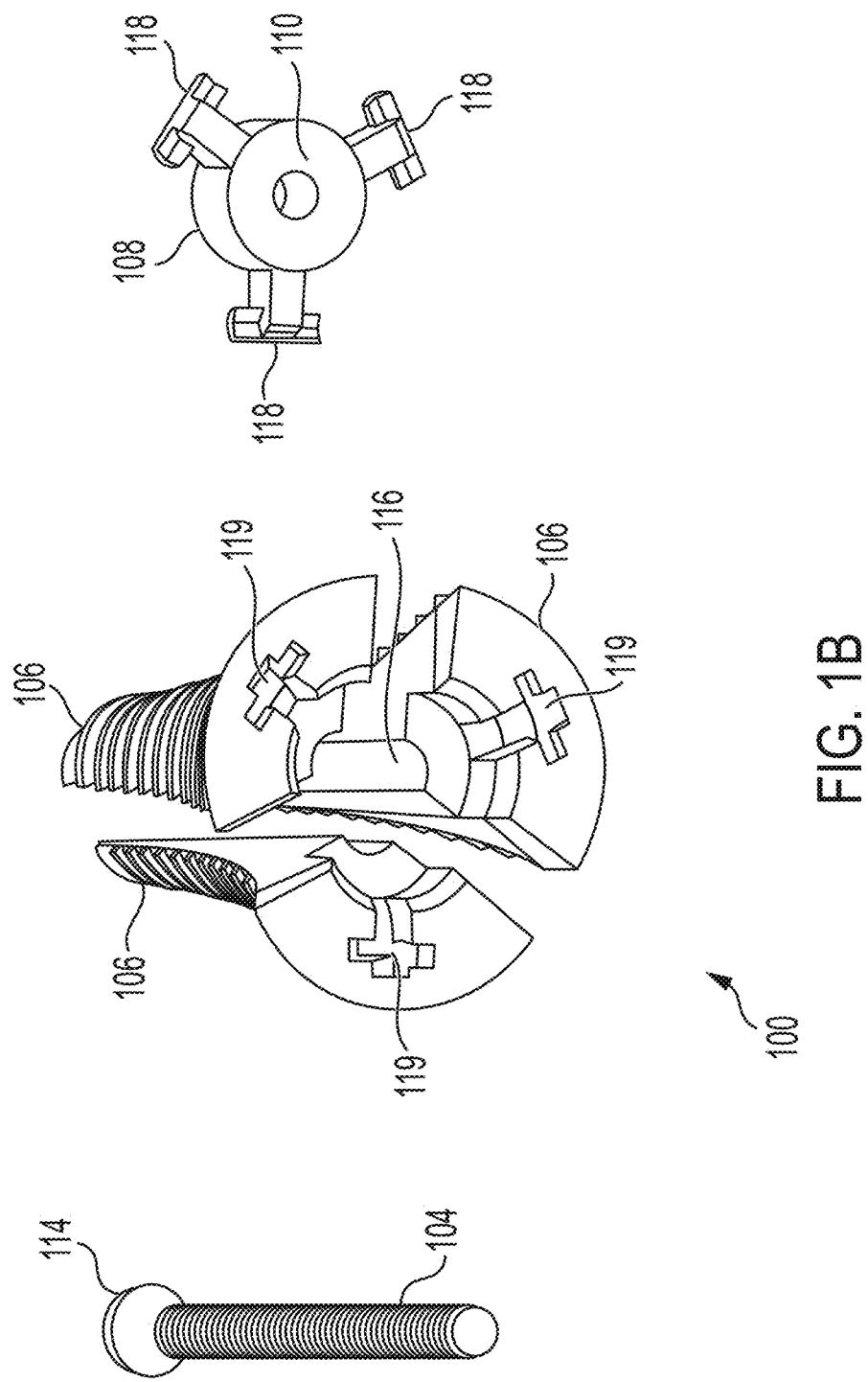
FIG. 1B is a perspective view of the components of a sinus tract expander, in accordance with some embodiments.

The following disclosure provides many different embodiments, or examples, for implementing different features of the provided subject matter. Specific examples of components, values, operations, materials, arrangements, etc., are described below to simplify the present disclosure. These are, of course, examples and are not intended to be limiting. Other components, values, operations, materials, arrangements, or the like, are contemplated. For example, the formation of a first feature over or on a second feature in the description that follows may include embodiments in which the first and second features are formed in direct contact and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIGS. 1A, 1B, 1C and 1D depict a tract expander system 100, in accordance with an embodiment. The tract expander system 100 includes an expander assembly 102, a hinged base 108 and a threaded shaft 104.

The expander assembly 102 is formed from a plurality of wings 106. Each wing 106 includes a central channel groove 116 (seen in FIG. 1B) along the spine of the wing 106, a drain channel 122 (FIG. 1B) and an exterior thread 120.

The hinged base 108 has a central threaded hole 110 (FIG. 1B). Between the wings 106 and the hinged base 108 are hinges 112 (seen in FIG. 4).

Each hinge 112 is formed from a hinge pin 118 on the hinged base 108 and a hinge knuckle 119 cut into the wing 106. The hinge base 108 and the wings 106 act as hinge leaves so that the rotation of the hinge pin 118 within the hinge knuckle 118 changes the angle between the hinge base 108 and a wing 106. The threaded shaft 104 has a tip 114 at one end. The diameter of the tip 114 is larger than the diameter of the threaded shaft 104.

The expander assembly 102 is formed from a plurality of wings 106. With the wings connected to the hinged base 108 and rotated on the hinges 112 so that the tops of the wings (the wing portion distal from the hinged base 108) are brought together, the expander assembly 102 has a conical shape in side view. In accordance with other embodiments, the expander assembly 102 has a cylindrical shape. In accordance with other embodiments, the expander assembly 102 has a shape appropriate to expand a passage, duct, canal, or the like.

In accordance with the embodiment depicted in FIGS. 1A, 1B, 1C and 1D, three wings 106 form the expander assembly 102. Each wing 106 is a curved wedge that forms ⅓ of the conical shape of the expander assembly 102. In accordance with other embodiments, the expander assembly 102 includes two, four, five or another suitable number of wings 106. Where the wings 106 are the same size, each of the wings 106 forms a proportionate portion of the circumference so that each of two wings 106 would make up one half (½) of the expander assembly 102, each of three wings 106 would make up one third (⅓) of the expander assembly 102, each of four wings 106 would make up one fourth (¼) of the expander assembly and so forth.

The exterior threads 120 on the wings 106, when the expander assembly 102 is assembled and closed, form a continuous thread around the circumference and along the length of the expander assembly 102. The exterior threads 120 assist the initial expander placement into the stenotic canal or passage by threading inwards against the walls of the canal/passage. The exterior threads 120 stabilizes the expander assembly 102 inside the canal/passage and prevents the expander assembly from falling outwards, at initial placement and with subsequent expansion. The exterior threads 120 have a pitch range of 0.8-2.0 mm, and a thread height range of 0.2-0.5 mm.

Each wing 106 includes a central channel groove 116 (FIG. 1B). The central channel groove 116 is a smooth indentation along the interior spine of the wing 106. With the expander assembly 102 assembled and closed, the central channel grooves 116 of the wings 106 form a smooth central channel 124 configured to surround the threaded shaft 104. As the expander assembly 102 is opened, the tip 114 of the threaded shaft 104 moves along the central channel grooves 116, spreading the wings 106 apart.

The threaded shaft 104 is a cylinder with exterior threads along the length. One end of the threaded shaft 104 screws into a threaded hole 110 in the hinged base 108. The other end of threaded shaft 104 has a tip 114. In accordance with some embodiments, the tip 114 includes a polymer. In accordance with some embodiments, the tip 114 includes a drug-eluting polymer. The diameter of the tip 114 is larger than the diameter of the threaded shaft 104. The tip 114 is formed of metal like the rest of the threaded shaft 104, polymer or substance coated, or a polymer overmolded onto the tip 114. The rounded/oval design of the tip 114 guides and assists the insertion as the tip 114 enters the stenotic canal/passage. In some embodiments, the tip 114 is sharpened or blunted.

In accordance with an embodiment, the threaded shaft 104 is formed from a rigid material. In accordance with other embodiments, the threaded shaft 104 is formed from a flexible material. The threaded shaft 104 is rotated using a tool such as a socket wrench, screwdriver or other appropriate tool.

Between the hinged base 108 and the wings 106 are three equidistantly spaced hinges 112 (seen in FIG. 4) formed by the hinge pins 118 on the hinged base 108 and the hinge knuckles 119 in the wings 106. The number of wings 106 equals the number of hinges 112. In accordance with other embodiments, the tract expander system 100 includes two, four, five or another appropriate number of hinges 112. The hinged base 108 includes central threaded hole 110 to receive the threaded shaft 104.

The hinges 112 include hinge pins 118 on the hinged base 108 and hinge knuckles 119 in the wings 106. The wings 106 and the hinged base 108 act as hinge leaves so that rotation of the hinge pin 118 within a hinge knuckle 119 causes a change in the angle between a wing 106 and the hinged base 108. The hinge pin 118 is inserted into the hinge knuckle 119 so that the hinge pin 118 rotates within the hinge knuckle 119, changing the angle between the wing 106 and the hinged base 108. Three hinge pins 118 are integrally formed equidistantly around the circumference of the hinged base 108. A hinge knuckle 119 is integrally formed in the wing 106.

In accordance with other embodiments, the hinges 112 include hinge leaves (not shown) that are attached to the wing 106 and hinged base 108. The hinges 112 include hinge pins 118 that are on the exterior of the hinged base 108. The hinges 112 include hinge knuckles 119 that are cut into the wings 106. In accordance with other embodiments, the hinges include hinge pins 118 that are on the exterior surface of the wings 106. The hinges include hinge knuckles 119 that are cut into the hinged base 108.

In accordance with other embodiments, the hinges 112 are hinge types that do not include hinge pins 118 or hinge knuckles 119. In accordance with some embodiments, the hinges 112 are strips of flexible material connected between the wings 106 and the hinged base 108.

FIG. 1A depicts a side view of the components of a tract expander system 100, in accordance with an embodiment. The tract expander system 100 includes an expander assembly 102, a threaded shaft 104 and a hinged base 108. The threaded shaft 104 includes a tip 114. The expander assembly 102 is formed from three wings 106. The three wings 106 include exterior threading that forms a continuous thread around the expander assembly 102.

FIG. 1B depicts a perspective view of the components of a tract expander system 100, in accordance with an embodiment. The tract expander system 100 includes an expander assembly 102, a threaded shaft 104 and a hinged base 108. The threaded shaft 104 includes a tip 114. The expander assembly 102 is formed from three wings 106. The base of each wing 106 includes a hinge knuckle 119. The interior of each wing 106 is concave along the spine of the wing 106 forming a central channel groove 116. The hinged base 108 has a threaded hole 110 through the center of the hinged base 108. On the exterior of the hinged base 108 are three hinge pins 118.

Figure 1C:
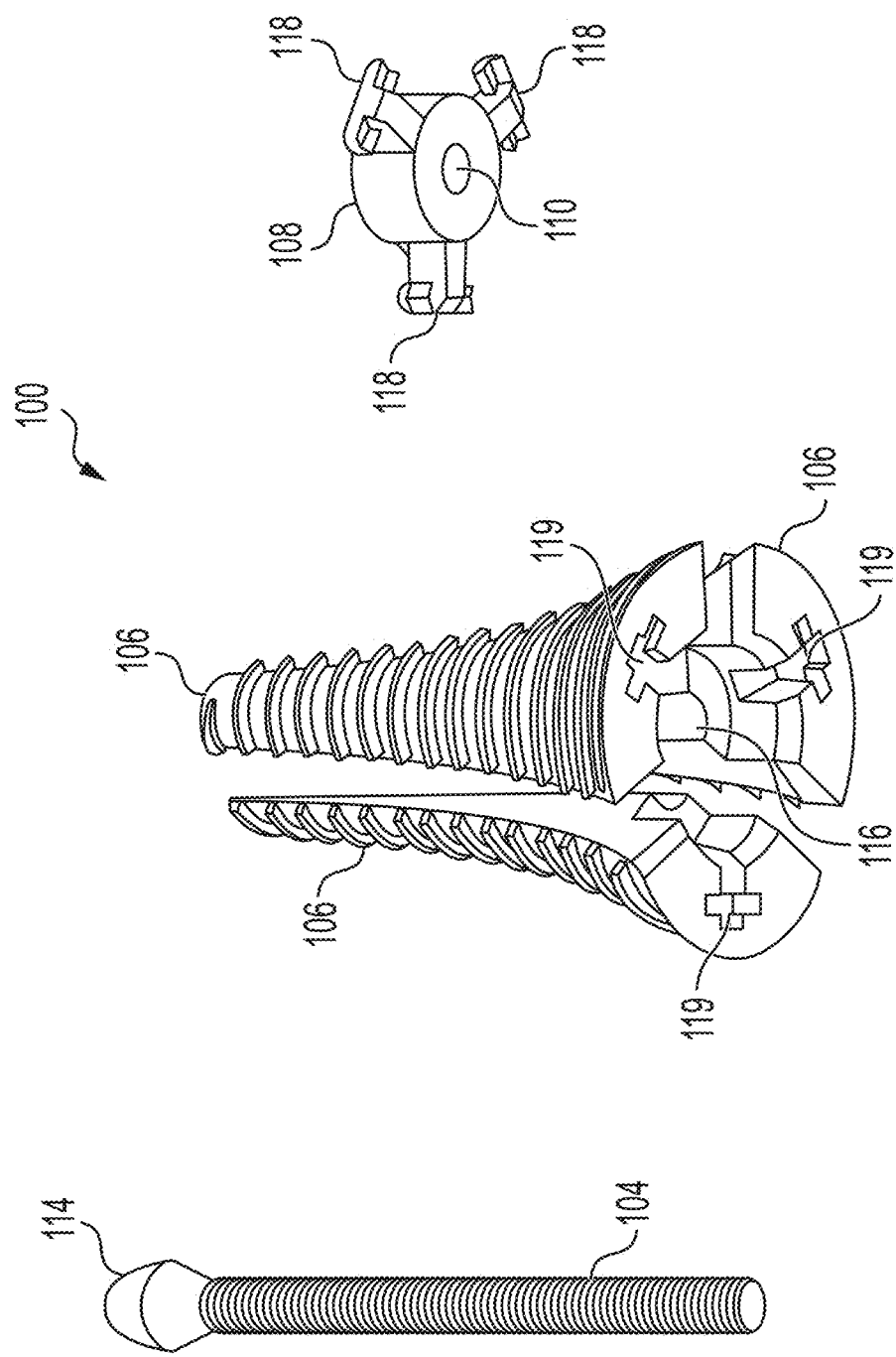
FIG. 1C is a perspective view of the components of a sinus tract expander, in accordance with some embodiments.

FIG. 1C depicts a perspective view of the components of a tract expander system 100, in accordance with an embodiment. The tract expander system 100 includes an expander assembly 102, a threaded shaft 104 and a hinged base 108. The threaded shaft 104 includes a tip 114. The expander assembly 102 is formed from three wings 106. The base of each wing 106 includes a hinge knuckle 119. The interior of each wing 106 is concave along the spine of the wing 106 forming a central channel groove 116. The hinged base 108 has a threaded hole 110 through the center of the hinged base 108. On the exterior of the hinged base 108 are three hinge pins 118.

Figure 1D:
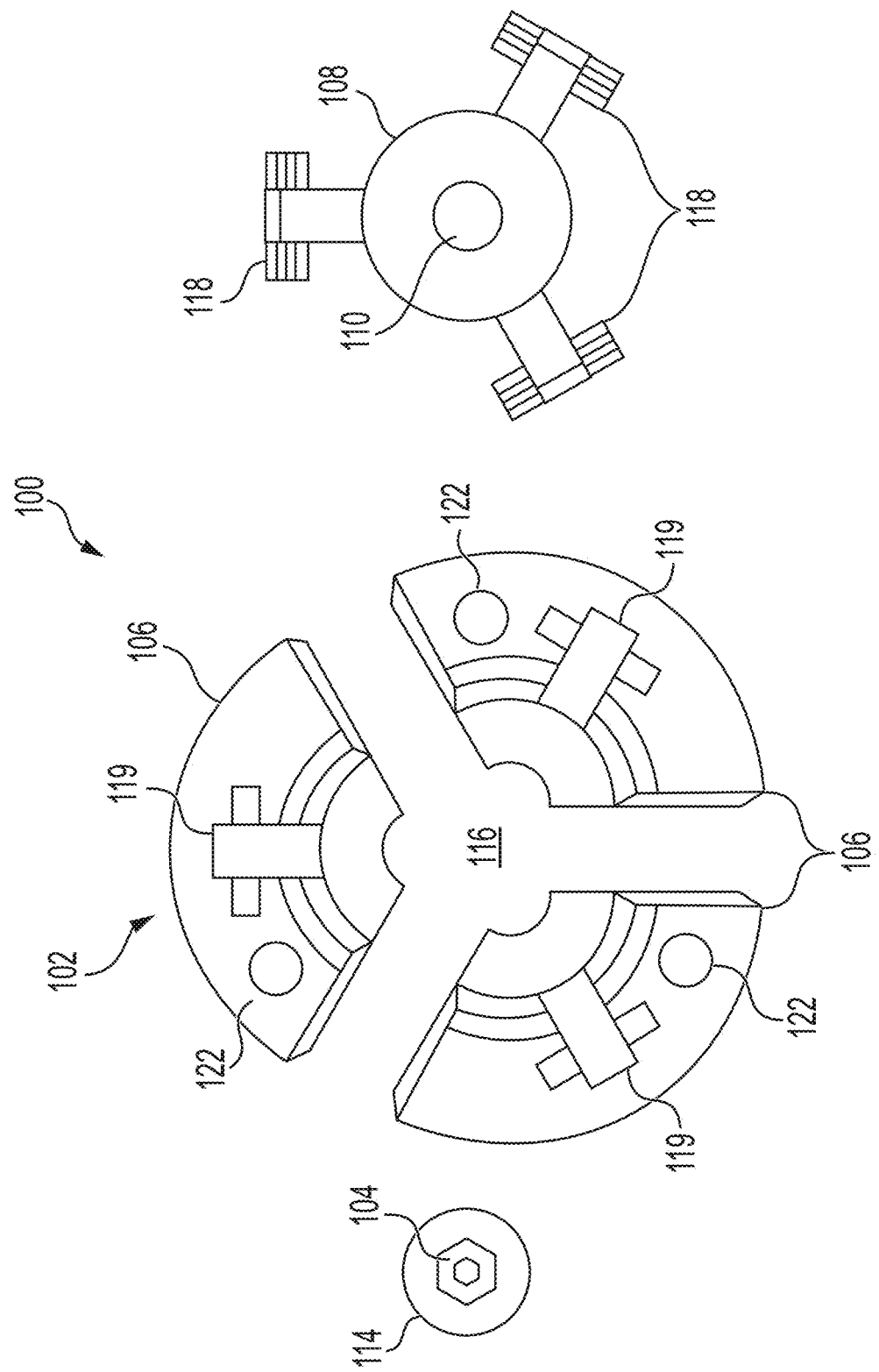
FIG. 1D is a bottom view of the components of a sinus tract expander, in accordance with some embodiments.

FIG. 1D depicts a bottom view of the components of a tract expander system 100, in accordance with an embodiment. The tract expander system 100 includes an expander assembly 102, a threaded shaft 104 and a hinged base 108. The threaded shaft 104 includes a tip 114. The expander assembly 102 is formed from three wings 106. The base of each wing 106 includes a hinge knuckle 119. The base of each wing 106 includes a drain channel 122. The interior of each wing 106 is concave along the spine of the wing 106 forming a central channel groove 116. The hinged base 108 has a threaded hole 110 through the center of the hinged base 108. On the exterior of the hinged base 108 are three hinge pins 118.

Figure 3B:
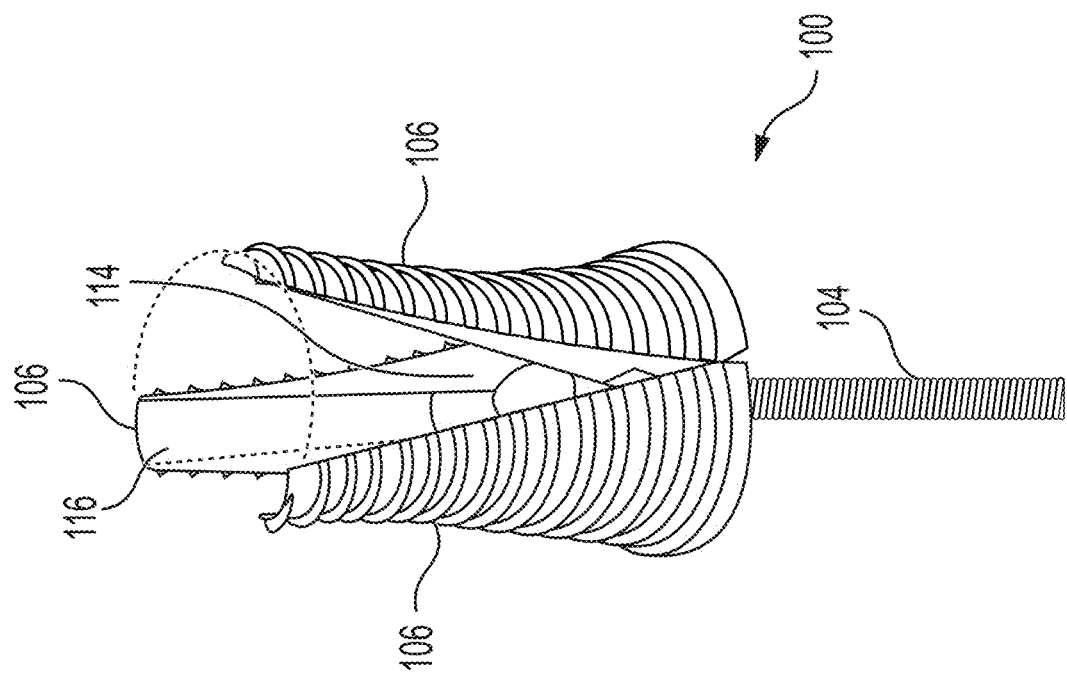
FIGS. 3A and 3B are perspective views of a sinus tract expander, in accordance with some embodiments.
Figure 3A:
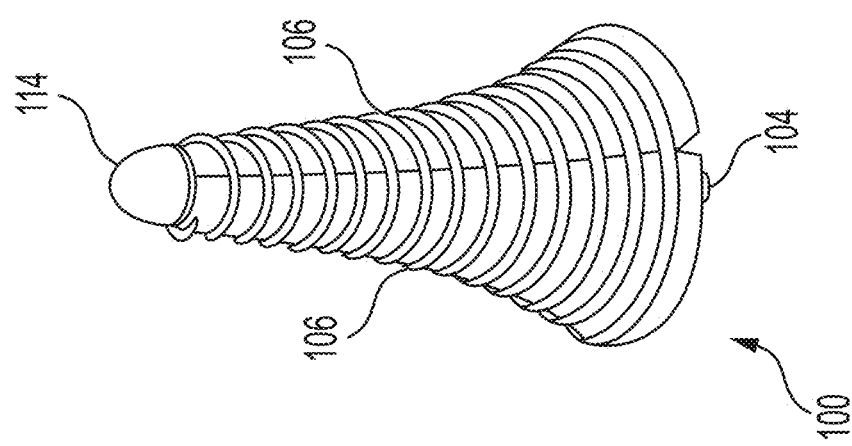
Figure 4B:
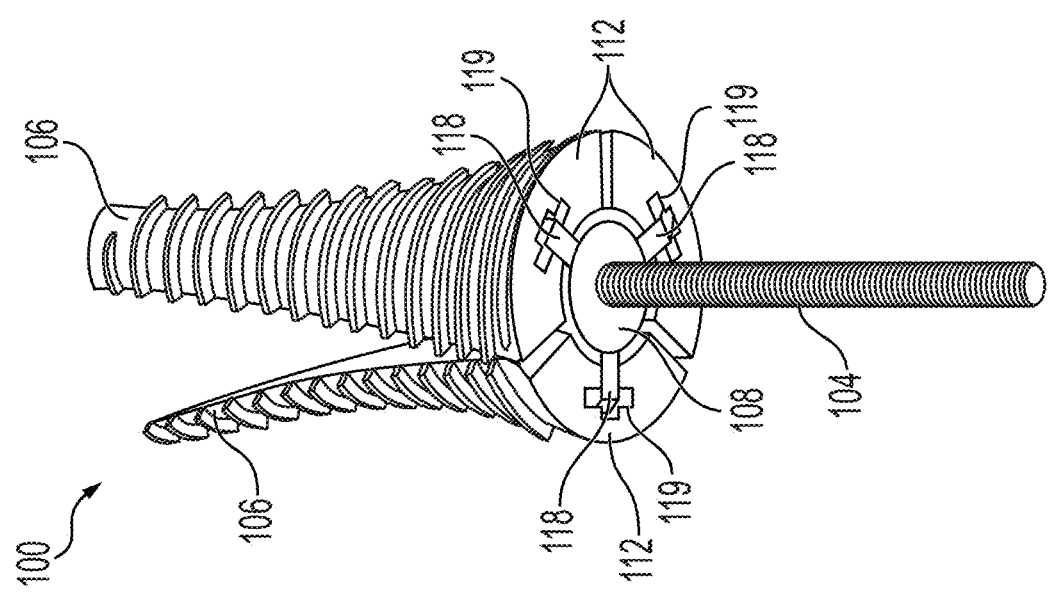
FIGS. 4A and 4B are perspective views of a sinus tract expander, in accordance with some embodiments.
Figure 4A:
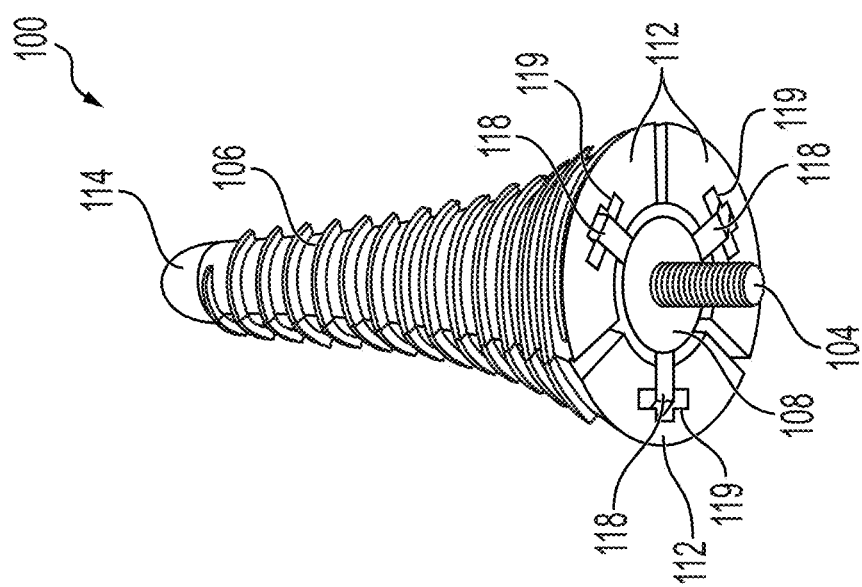

FIGS. 2A, 2B, 3A, 3B, 4A and 4B depict the tract expander system 100 in accordance with some embodiments. FIG. 2A is a side view of the tract expander system 100 in a closed position. FIG. 2B is a side view of the tract expander system 100 in an open position, i.e., having the wings rotated around hinges 118. FIG. 3A is a perspective view of the tract expander system 100 in a closed position. FIG. 3B is a perspective view of the tract expander system 100 in an open position, i.e., having the wings rotated around hinges 118. FIG. 4A is a perspective view of the tract expander system 100 in a closed position. FIG. 4B is a perspective view of the tract expander system 100 in an open position, i.e., having the wings rotated around hinges 118.

By rotating the threaded shaft 104, the threaded shaft 104 moves through the threaded hole 110 of the hinged base 108.

The resulting movement of the tip 114 toward the hinged base 108 pushes the tops of the wings 106 apart, increasing the circumference of the upper end of the expander assembly 102.

The threaded shaft 104 is rotated until the expander assembly 102 is in a maximally expanded position, gradually expanding from, for example, a circumference measured around the tips of the wings 106 (circumference (c) in FIG. 2A) of 3.00 mm to 11.4 mm over a period of weeks to months. In accordance with an embodiment, periodic expansion is performed after placement every 1-2 weeks, with an increase of diameter of 1-3 mm (measured at wing tip) per expansion, as tolerated by the patient. When rotated, the threaded shaft 104 pulls the tip 114 down the central channel grooves 116 that formed the central channel 124 so that the central channel grooves 116 spread apart. Because the tip 114 has a larger diameter than the threaded shaft 104, the tip 114 presses against the central channel grooves 116 as the tip 114 descends, causing the top of the wings 106 to move outwardly away from the threaded shaft 104.

In use, as the threaded shaft is rotated, the tip 114 descends toward the hinged base 108 and presses against the central channel grooves 116, the wings 106 rotate away from the threaded shaft 104 on the hinges 112 so that the tops of the wings 106 separate and enlarge the circumference of the expander assembly 102 from a closed cone to an opened cone.

The expander assembly 102 is assembled by inserting the hinge pins 118 into the hinge knuckles 119 of the wings 106 and rotating the wings 106 upward.

In accordance with some embodiments, the height (a) of the expander assembly 102 and the polymer tip 114 is 22.50 mm, with a range of 10 mm-40 mm. The height (b) of the expander assembly 102 is 19.75 mm, with a range of 8 mm to 37 mm. The circumference (c) of the polymer tip 114 is 3.00 mm, with a range of 1 mm to 4.5 mm The circumference (d) of the threaded shaft 104 is 1.6 mm, with a range of 1 mm to 2.5 mm The circumference of the base of the expander assembly 102 is 12.00 mm, with a range of 7 mm to 20 mm. The height (f) of the expander assembly 102 and the threaded shaft 104, when fully open is 39.07 mm, with a range of 25 mm to 50 mm In accordance with other embodiments, other dimensions are implemented as required by the therapies.

The expander assembly 102 is expanded circumferentially to provide incrementally increased pressure against a sinus tract, a stenotic bony canal or a duct of a patient. The circumference of the expander assembly 102 is forcibly increased over time to expand the opening of the bony canal.

The expander assembly 102 is formed from three threaded wings 106. Each of the wings 106 includes a hinge knuckle 119. The hinge knuckle 119 is connected to a hinge 112 on the hinged base 108. Each of the three threaded wings 106 is a curved triangular shape with partial threads on the outer surface of the threaded wings 106. The three threaded wings 106 are connected to the hinges 112 of the hinged base 108 so that the three threaded wings 106 rotate from a closed position, as shown in FIGS. 2A, 3A and 4A to an open position, as shown in FIGS. 2B, 3B and 4B. With the expander assembly 102 in a closed position, as shown in FIGS. 2A, 3A and 4A, the expander assembly 102 has an externally threaded conical shape and an internal central channel.

The expander 102 is expanded by rotation of the threaded shaft 104 into the threaded hole 110 of the hinged base 108. The threaded hole 110 receives the threaded shaft 104. As the threaded shaft 104 is rotated, the tip 114 of the threaded shaft 104 descends toward the hinged base 108 and spreads the wings 106 apart, increasing the circumference of the expander 102 so that the expander 102 presses against the bony canal.

The tract expander system 100 includes a hinged base 108 with three hinge pins 118 and three wings 106 with three hinge knuckles 119 that attach to the three hinge pins 119. The centrally mounted threaded shaft 104 is threaded into the hinged base 108 at one end of the threaded shaft 104, and another end having a conical shape supporting the drug-eluting polymer tip 114.

In accordance with some embodiments, the wings 106, hinged base 108 and threaded shaft 104 are made from a rigid material, such as titanium Grade 5 (Ti6Al4V), 316L stainless steel, a biocompatible resorbable polymer like polylactic acid/polyglycolic acid, or another appropriate material.

The drug-eluting polymer tip 114 is a conical end of the threaded shaft 104 and contains a drug eluting polymer (PLGL: Poly-(DL-lactide-co-glycolide)). The drug eluting polymer dissolves via hydrolysis over a period of approximately 90 days. The drug-eluting polymer tip 114 releases steroid medication (such as 800-1000 μg mometasone furoate, a highly lipophilic steroid) to prevent scarring and inflammation at the site of the expanded sinus tract, as well as treat the disease process in the area.

The drug-eluting polymer tip 114, in accordance with various embodiments, includes any medication or substance, or combinations of medications and substances thought to facilitate ideal healing, prevent infection, or reduce pain. In accordance with various embodiments, the drug-eluting polymer tip 114 includes inactive ingredients that assist in binding the medication to the polymer or increasing its stability.

The sinus tract expander 100 is particularly useful in methods of treating the Frontal sinus, the Sphenoid sinus, Maxillary sinus, the Eustachian tube, auditory canal (external auditory meatus) or another appropriate feature.

The sinus tract expander 100 is used in methods of treating any stenotic (narrowed) bony canal or duct. The stenotic bony canal expander 100 is especially effective in locations of the body where the bony canal does not conduct a nerve or blood vessel, locations without structures that risk being crushed.

The tract expander system 100, in accordance with some embodiment, is used to treat the mucosa, the tissue surrounding and covering the bony areas of the sinus. The polymer tip 114 of the tract expander system 100 includes a dissolvable polymer impregnated with a therapeutic dose of steroids. For example, in accordance with an embodiment, a steroid medication is delivered at a very low dose (400-600 micrograms total quantity), or a low dose (600-800 micrograms) or a medium dose (800-1000 micrograms) or a high dose (1000-1200 micrograms). Other medications require different dosage quantities, appropriate to the specific medication. As the polymer dissolves/resorbs, the dose of steroid is released and mitigates mucosal swelling from the surgery, the device itself, or the underlying disease process.

Figure 5:
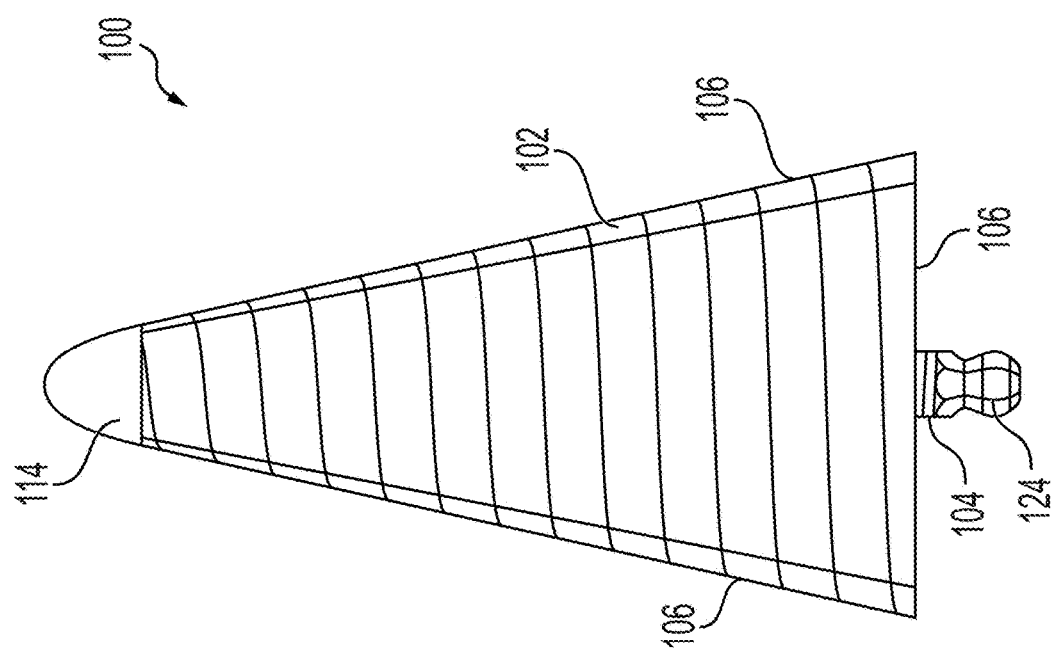
FIG. 5 is a side view of a tract expander system, in accordance with some embodiments.

FIG. 5 depicts a tract expander system 100 in accordance with another embodiment. An expander assembly 102 is formed from a plurality of wings 106. When the wings are connected to the hinged base 108 and rotated on the hinges 112 so that the tops of the wings 106 are brought together, the expander assembly 102 has a truncated conical shape with a constant slope from the tops of the wings 106 to the bottoms of the wings 106 along the exterior. The constant slope provides a wide variety of circumferences for the expander assembly 102 around the tops of the wings 106 to engage the passage, as compared to the expander assembly 102 shown in FIGS. 1A and 2A.

Within the expander assembly 102 is the threaded shaft 104. Extending above the expander assembly 102, fixed to the threaded shaft 104 is tip 114. The threaded shaft 104, below the expander assembly 102, has the shape of a hex key 124 so that the threaded shaft 104 can be rotated with a socket wrench (not shown).

Figure 6:
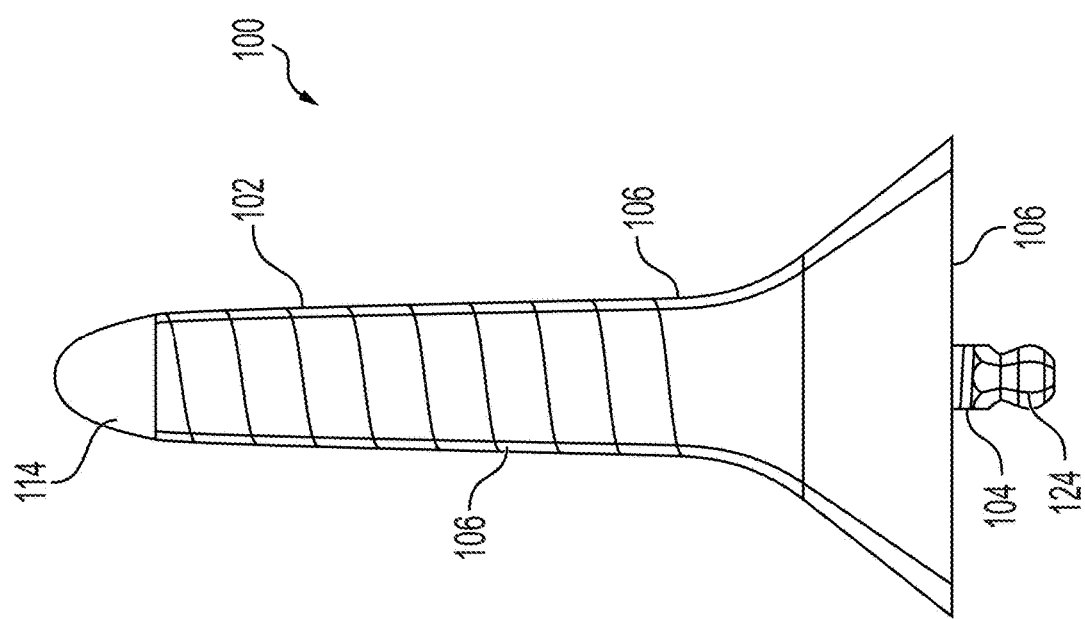
FIG. 6 is a side view of a tract expander system, in accordance with some embodiments.

FIG. 6 depicts a tract expander system 100 in accordance with another embodiment. The expander assembly 102 has a straight cylindrical shape with a flared base. The expander assembly 102 is formed from a plurality of wings 106. When the wings are connected to the hinged base 108 and rotated on the hinges 112 so that the tops of the wings 106 are brought together, the expander assembly 102 has a cylindrical shape along the exterior. The cylindrical shape provides deeper penetration for the expander assembly 102 to engage the sinus passage, as compared to the expander assembly 102 shown in FIGS. 1A and 2A.

Within the expander assembly 102 is the threaded shaft 104. Extending above the expander assembly 102, fixed to the threaded shaft 104 is tip 114. The threaded shaft 104, below the expander assembly 102, has the shape of a hex key 124 so that the threaded shaft 104 can be rotated with a socket wrench (not shown).

Figure 7:
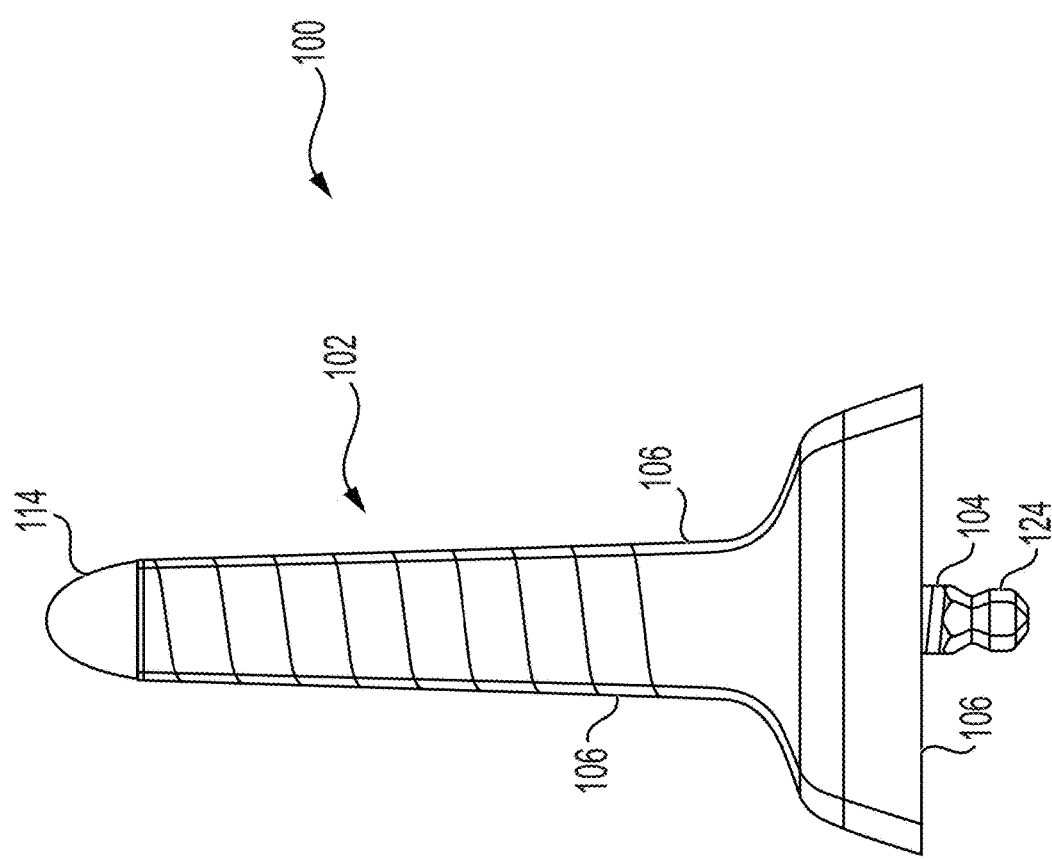
FIG. 7 is a side view of a tract expander system expander assembly, in accordance with some embodiments.

FIG. 7 depicts a tract expander system 100 in accordance with another embodiment. The expander assembly 102 has a straight cylindrical shape with a flared base. The expander assembly 102 is formed from a plurality of wings 106. When the wings are connected to the hinged base 108 and rotated on the hinges 112 so that the tops of the wings 106 are brought together, the expander assembly 102 has a cylindrical shape along the exterior. The cylindrical shape provides deeper penetration for the expander assembly 102 to engage the sinus passage, as compared to the expander assembly 102 shown in FIGS. 1A and 2A.

Within the expander assembly 102 is the threaded shaft 104. Extending above the expander assembly 102, fixed to the threaded shaft 104 is tip 114. The threaded shaft 104, below the expander assembly 102, has the shape of a hex key 124 so that the threaded shaft 104 can be rotated with a socket wrench (not shown).

Figure 8:
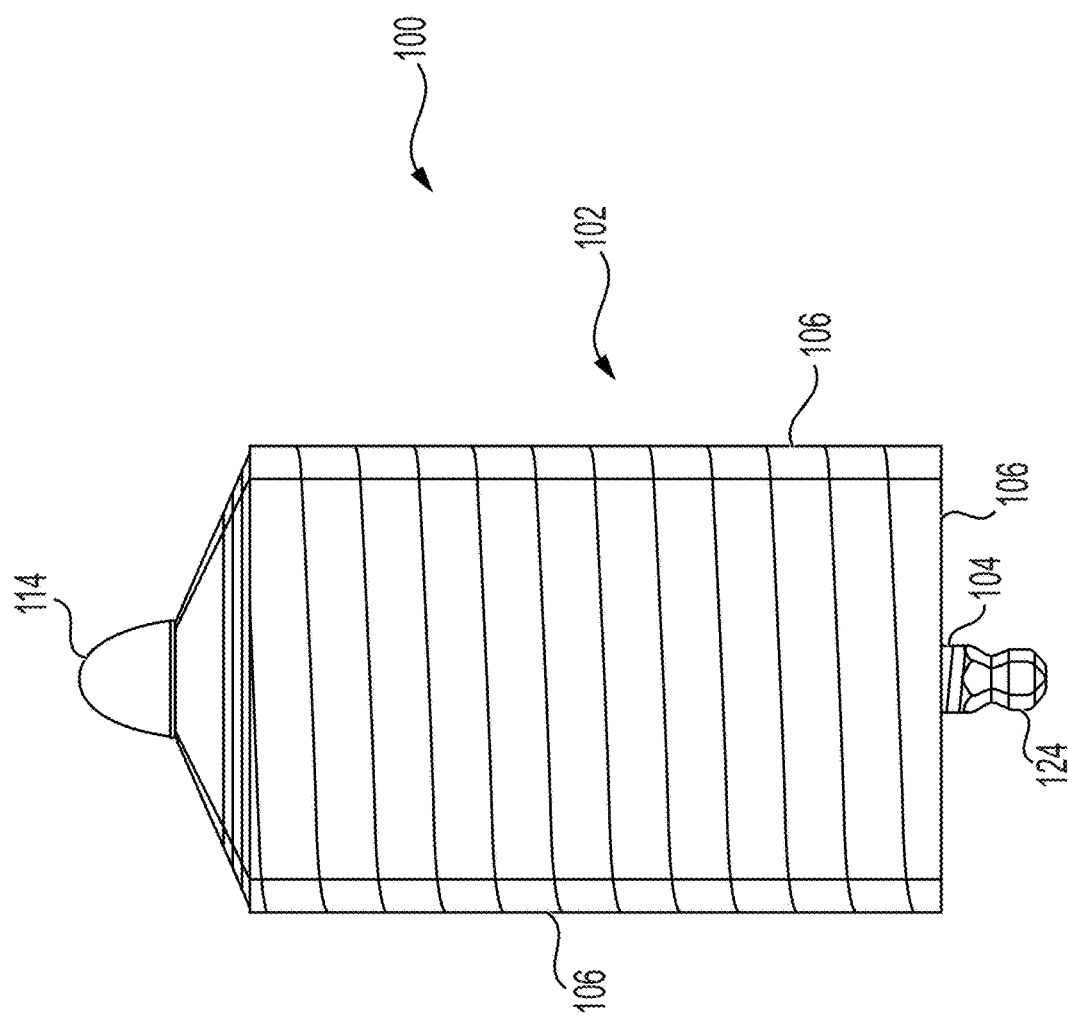
FIG. 8 is a side view of a tract expander system expander assembly, in accordance with some embodiments.

FIG. 8 depicts a tract expander system 100 in accordance with another embodiment. The expander assembly 102 has a wide cylindrical shape. The expander assembly 102 is formed from a plurality of wings 106. When the wings are connected to the hinged base 108 and rotated on the hinges 112 so that the tops of the wings 106 are brought together, the expander assembly 102 has a cylindrical shape along the exterior. The wide cylindrical shape provides deeper penetration for the expander assembly 102 to engage a larger sinus passage, as compared to the expander assembly 102 shown in FIGS. 1A and 2A.

Figure 13:
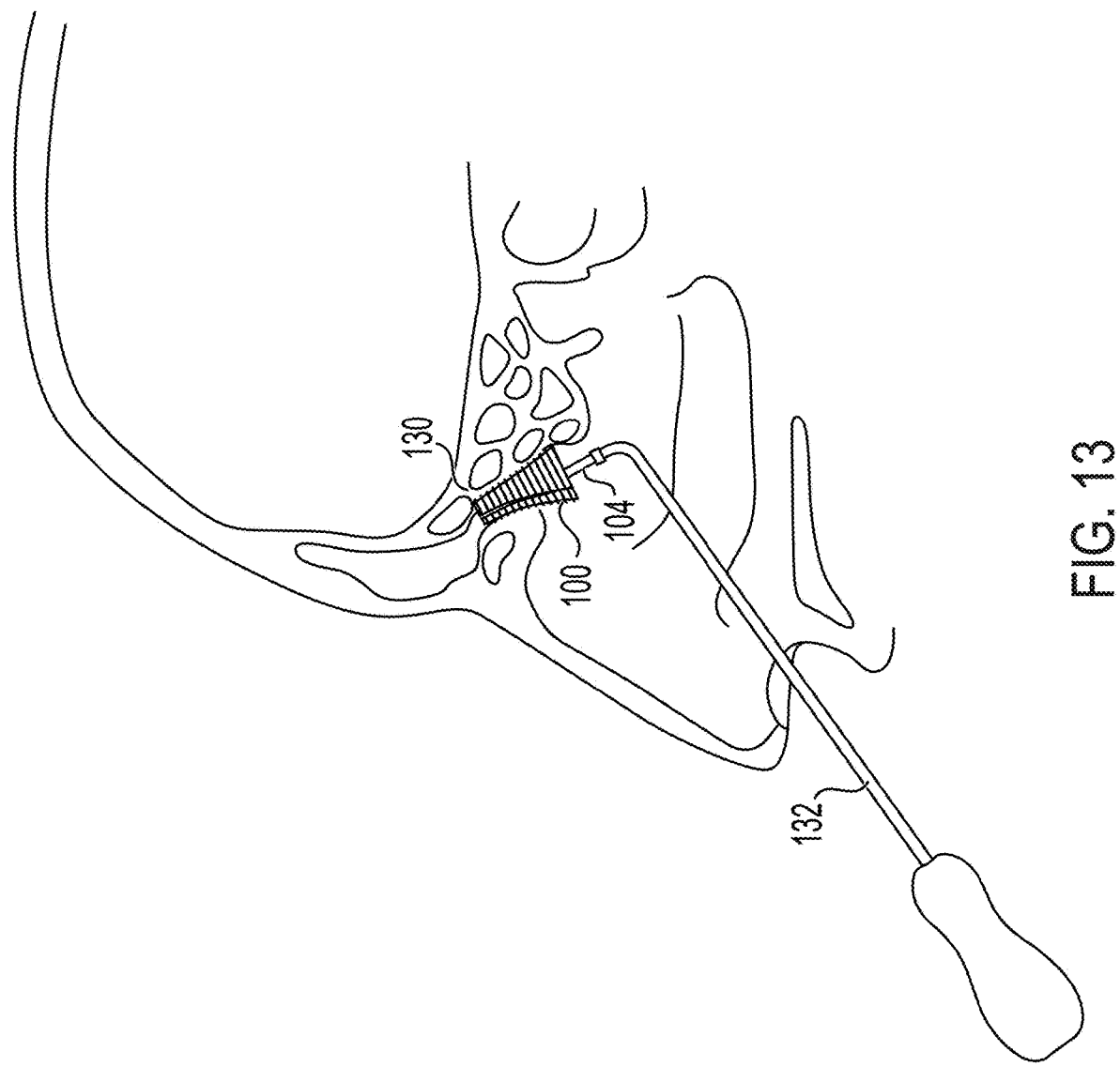
FIG. 13 depicts a tract expander installed in a sinus passage, in accordance with some embodiments.
Figure 14:
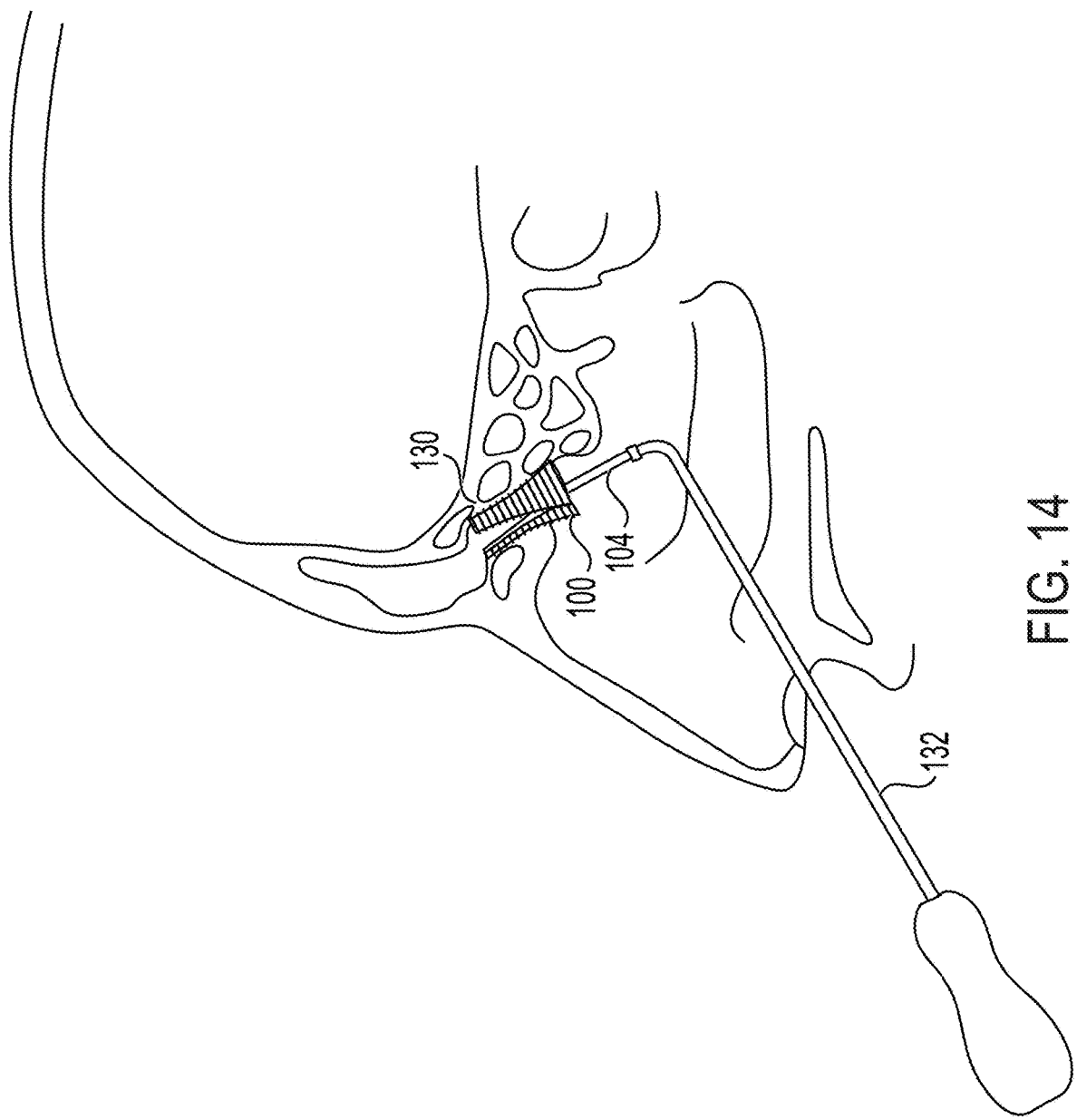
FIG. 14 depicts a tract expander installed in a sinus passage, in accordance with some embodiments.

Within the expander assembly 102 is the threaded shaft 104. Extending above the expander assembly 102, fixed to the threaded shaft 104 is tip 114. The threaded shaft 104, below the expander assembly 102, has the shape of a hex key 124 so that the threaded shaft 104 can be rotated with a socket wrench 132 as shown in FIGS. 13 and 14.

Figure 9:
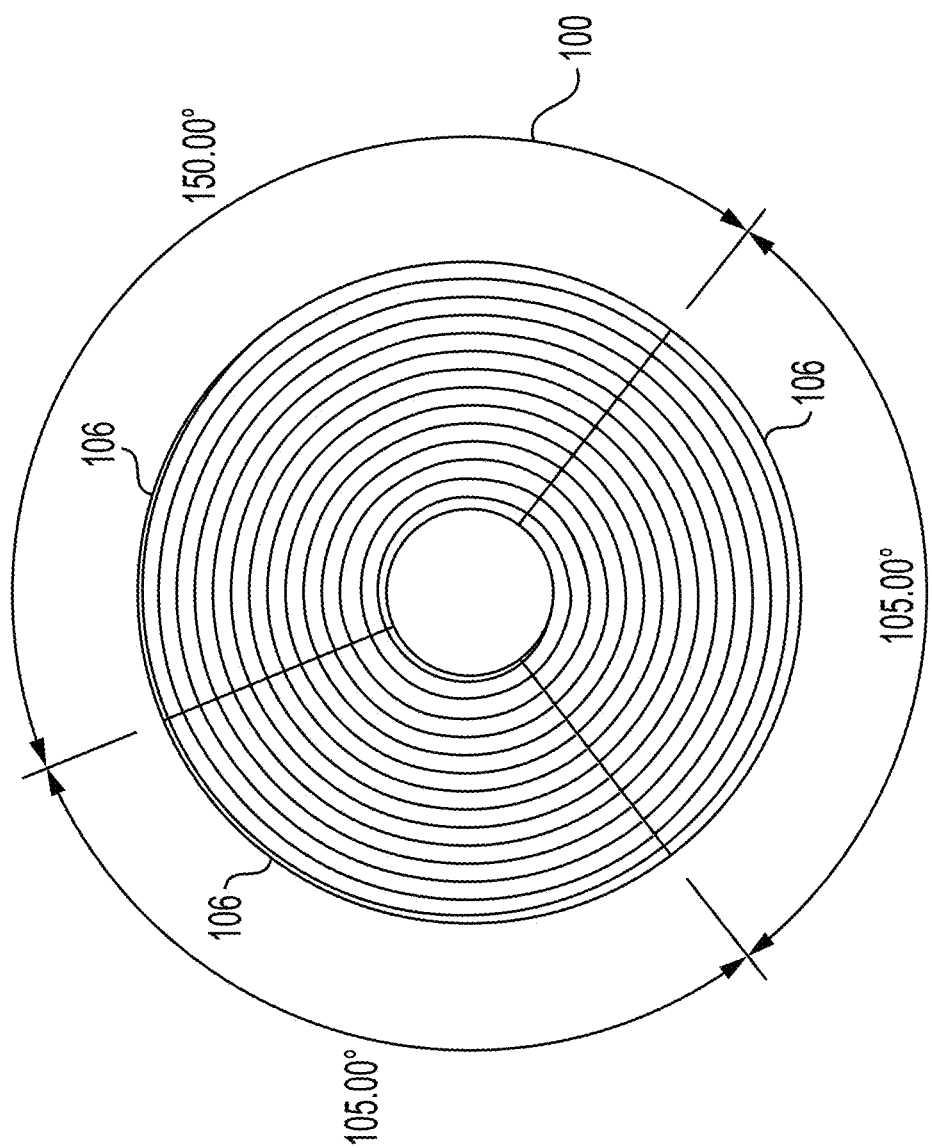
FIG. 9 is a top view of a tract expander assembly with unequal wings, in accordance with some embodiments.

FIG. 9 depicts a top view of an expander assembly 102, in accordance with an embodiment. The wings 106 are different sizes, so that each wing 106 makes up a portion of the expander assembly 102 circumference, where the portions are not necessarily equal, for example one larger wing 106 of 150.00° combined with two smaller wings 106 of 105.00°. The unequal wing sizes are utilized when the passage being expanded has irregular features.

Figure 10:
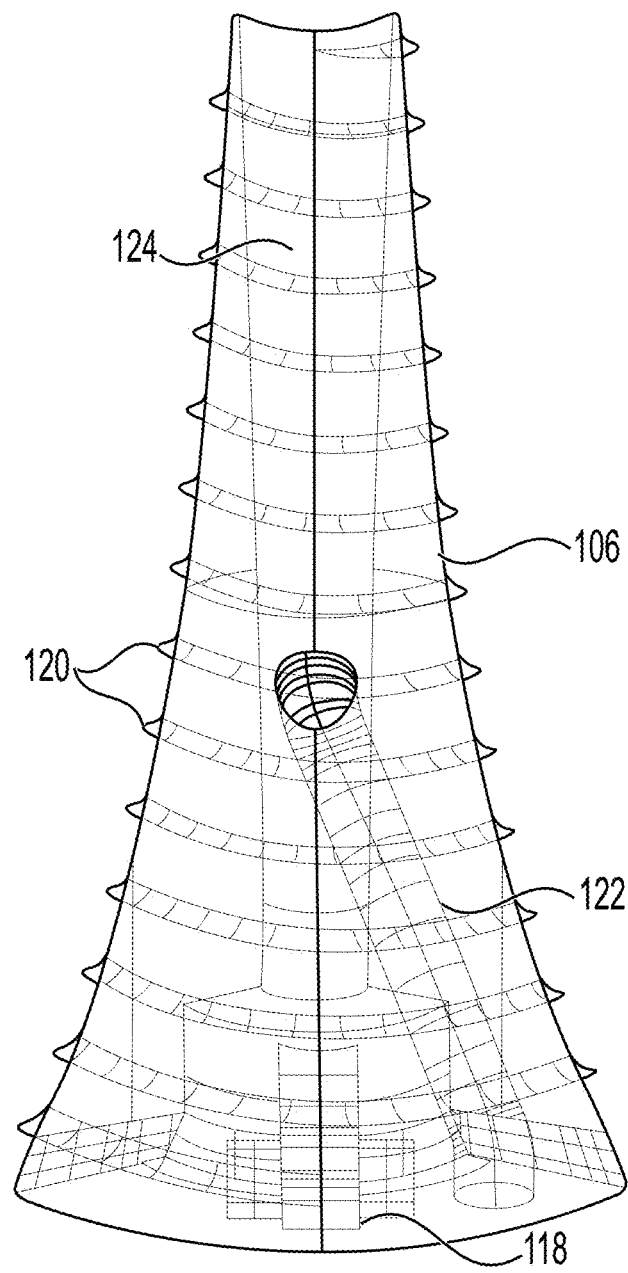
FIG. 10 is a side view of a wing, in accordance with some embodiments.

FIG. 10 depicts a wing 106 with a drain channel 122, in accordance with some embodiments. One or more of the wings 106 includes a drain channel 122 for flushing and draining the tract expander 100 while installed. The drain channel 122 is a cylindrical shaft from the base of the wing 106 to the interior of the wing 106. In accordance with an embodiment, the drain channel 122 has a diameter of 1.25 mm, with a range of 0.75-1.75 mm. In accordance with an embodiment, the drain channel 122 has a length of 9-15 mm, depending on position. The drain channel 122 is positioned along the central channel 116, or on either side of the wings 106. In accordance with various embodiments, the drain channel 122 is positioned higher or lower on the interior of the wing 106 The three drain channels 122 on the base of the wings 106 of the assembled tract assembly 102 are configured to engage a three-pronged installation tool, such as installation tool 128 as shown in FIG. 12, for installation of the tract expander system 100 in the sinus passage.

Figure 11:
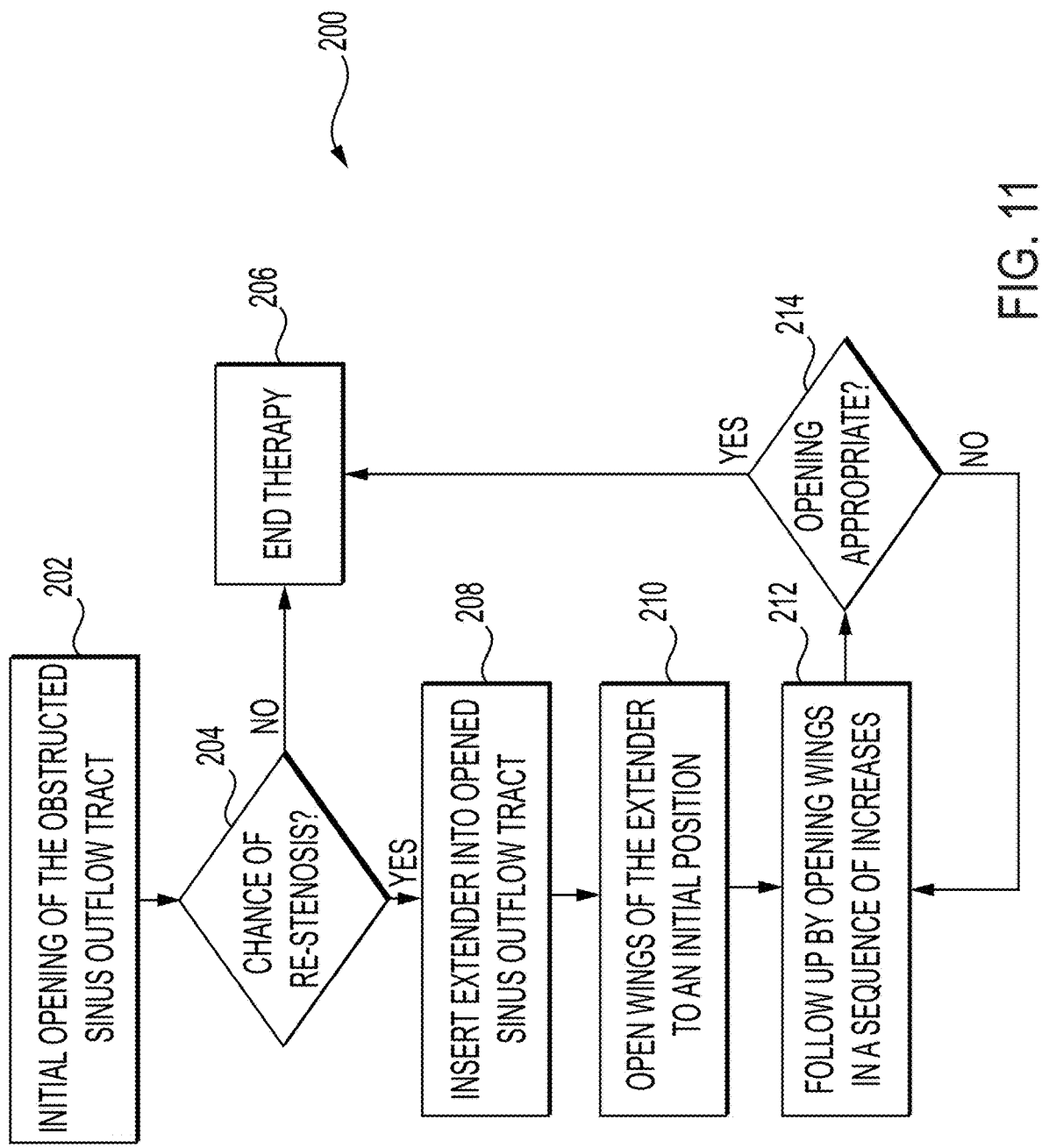
FIG. 11 is flow chart of a method of treating a stenotic sinus passage, in accordance with some embodiments.

FIG. 11 is a flowchart of a process 200 of treating an obstructed sinus outflow tract, in accordance with an embodiment. At step 202, an initial opening is made in an obstructed sinus outflow tract to enlarge the sinus passage. This procedure could be performed in the operating room or in the office using available standard techniques. The surgeon determines, at decision step 204, if there is a significant chance of re-stenosis and if an optimal opening would be larger. If there is no significant chance of re-stenosis and the opening is sufficient, the process ends at step 206. If there is a significant chance of re-stenosis and an optimal opening would be larger, the surgeon inserts the tract expander 100 having the wings in a closed position into the opened sinus outflow tract at step 208. The wings 106 of the canal extender 100 are opened to an initial position at step 210. At periodic time intervals, the wings 106 of the canal extender 100 are opened incrementally at step 212 to further open the tract by pushing the bone in much the same way braces move teeth. The diameter of the opening is checked at decision step 214. With the opening appropriately enlarged, the treatment is ended at step 206. If the opening is not appropriately enlarged, the process returns for further follow up at step 212.

In accordance with an embodiment, if the canal/passage is sufficiently large to permit the tip 114 and some part of the expander assembly 102 to enter the canal/passage, the expander assembly 102 is placed directly into the canal/passage without the initial opening of step 202, and then proceeding directly to the step 208.

Figure 12:
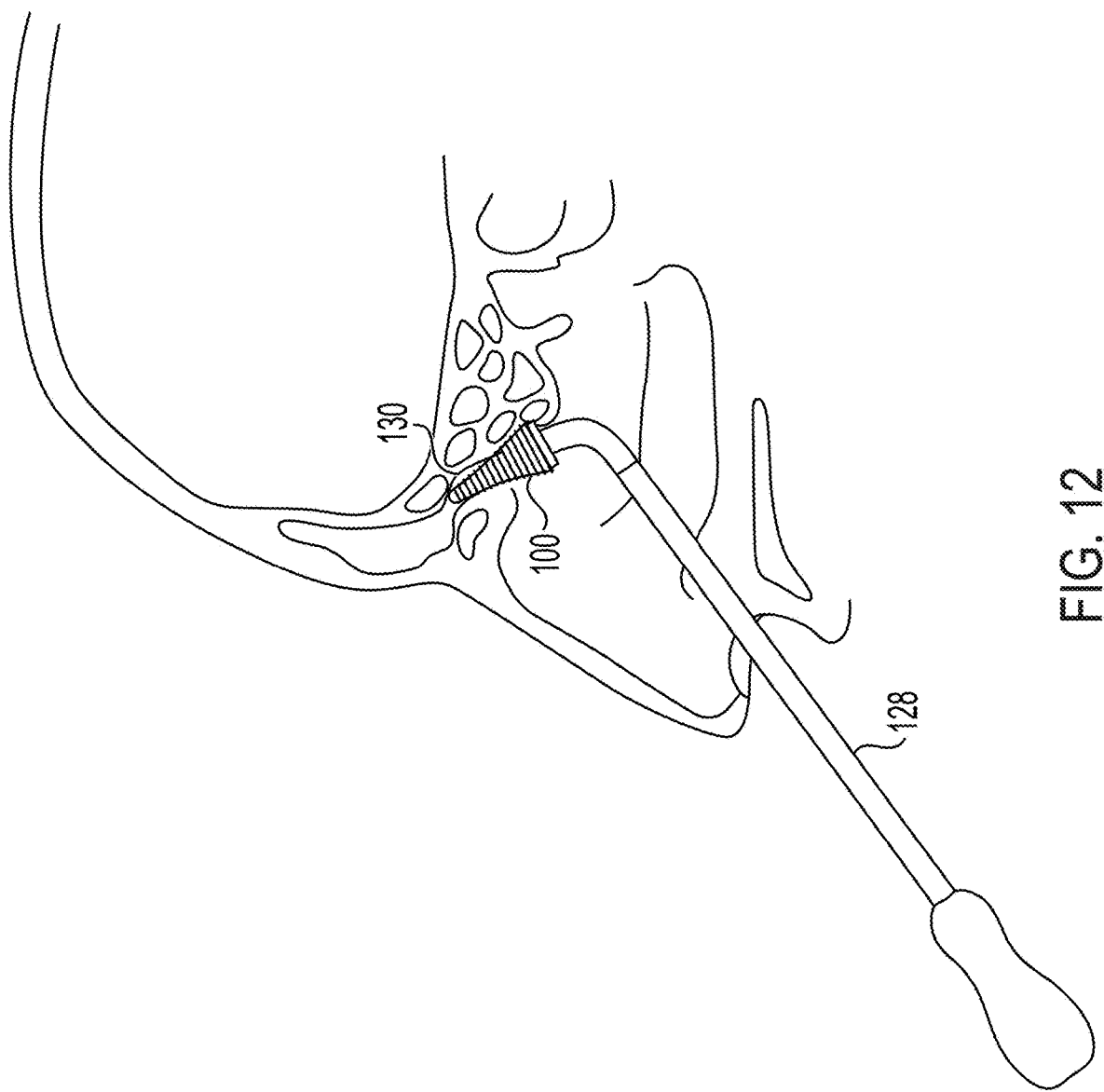
FIG. 12 depicts a tract expander installed in a sinus passage, in accordance with some embodiments.

FIG. 12 depicts a tract expander 100 as it is installed in a sinus passage 130. An installation tool 132, such as a three-pronged tool, is fixed to the base of the tract expander 100 and moved into position within the sinus passage 130. The installation tool 132 is removed when the tract expander 100 is situated within the sinus passage 130.

FIG. 13 depicts a tract expander 100 installed in sinus passage 130. A rotation tool 132 is connected to the threaded shaft 104 and used to rotate the threaded shaft 104 within the tract expander 100, causing the wings 106 to spread apart and apply pressure to the sinus passage 130.

FIG. 14 depicts a tract expander 100 installed in sinus passage 130. A rotation tool 132 is connected to the threaded shaft 104 and used to rotate the threaded shaft 104 within the tract expander 100, causing the wings 106 to spread apart and apply pressure to the sinus passage 130. As shown, the tract expander 100 is opened to the position required for expanding the sinus passage. The rotation tool 132 is removed when the tract expander 100 is opened. After a period of time, for example several days or weeks, the threaded shaft 104 is again rotated using the rotation tool 132 to further open the tract expander 100 and apply additional pressure to the sinus passage 130.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A tract expander comprising:
    a base having a threaded central hole and a plurality of hinge pins;
    a plurality of wings;
    a plurality of hinges wherein each of the plurality of hinges is connected to the base by receiving a corresponding hinge pin of the plurality of hinge pins, and to a wing of the plurality of wings so that each wing moves relative to the base; and
    a threaded shaft including a tip, wherein a diameter of the tip is larger than a diameter of the threaded shaft and wherein the threaded shaft is configured to screw into the threaded central hole;
    wherein the threaded shaft is configured to rotate and move the tip toward the base, causing tops of the plurality of wings to move away from the threaded shaft.

2. The tract expander of claim 1, wherein the tip is a polymer tip.

3. The tract expander system of claim 2 wherein the polymer tip is a drug-eluting polymer tip.

4. The tract expander system of claim 3, wherein the drug-eluting polymer tip is configured to release a steroid medication.

5. The tract expander system of claim 1 wherein the plurality of wings is three wings.

6. The tract expander system of claim 1 wherein the plurality of wings in a closed position have a conical shape.

7. The tract expander system of claim 1 wherein each wing of the plurality of wings defines a drain channel from a bottom of each wing to an interior side of each wing.

8. A tract expander system comprising:
    a hinged base having a plurality of hinge pins and a threaded central hole;
    a plurality of wings, wherein each wing includes a top and a bottom and wherein the bottom of each wing includes a hinge knuckle and a wing of the plurality of wings rotatably engages a hinge pin of the plurality of hinge pins with a corresponding hinge knuckle of the plurality of hinge knuckles; and
    a threaded shaft including a tip, wherein a diameter of the tip is larger than a diameter of the threaded shaft and wherein the threaded shaft is configured to screw into the threaded central hole;
    wherein the threaded shaft is configured to rotate and move the tip toward the hinged base, causing the tops of the plurality of wings to move away from the threaded shaft.

9. The tract expander system of claim 8, wherein an exterior edge of each wing has a constant slope.

10. The tract expander system of claim 8 wherein the plurality of wings in a closed position has a cylindrical shape.

11. The tract expander system of claim 8, wherein the wings are formed of titanium or stainless steel.

12. The tract expander system of claim 8 wherein at least one of the plurality of wings is larger than another of the plurality of wings.

13. The tract expander system of claim 8 wherein the tract expander system is installed using a three-pronged tool.

14. The tract expander system of claim 8 wherein the threaded shaft is rotated using a socket tool.

* * * * *